United States Patent
Manus et al.

(10) Patent No.: US 12,343,414 B2
(45) Date of Patent: Jul. 1, 2025

(54) ORAL CARE COMPOSITIONS AND METHODS OF USE

(71) Applicant: Colgate-Palmolive Company, New York, NY (US)

(72) Inventors: Lisa Marie Manus, Lawrenceville, NJ (US); Jonghun Lee, Metuchen, NJ (US); Joseph Allan McKinnon Steele, Plainfield, NJ (US); Shaopeng Xu, Guangzhou (CN); Yuzhi Deng, Guangzhou (CN)

(73) Assignee: Colgate-Palmolive Company, New York, NY (US)

( * ) Notice: Subject to any disclaimer, the term of this patent is extended or adjusted under 35 U.S.C. 154(b) by 540 days.

(21) Appl. No.: 17/765,382

(22) PCT Filed: Mar. 3, 2022

(86) PCT No.: PCT/CN2022/078926
§ 371 (c)(1),
(2) Date: Mar. 30, 2022

(87) PCT Pub. No.: WO2022/184115
PCT Pub. Date: Sep. 9, 2022

(65) Prior Publication Data
US 2023/0190595 A1    Jun. 22, 2023

(30) Foreign Application Priority Data

Mar. 5, 2021 (CN) .......................... 202110248821.7

(51) Int. Cl.
| | | |
|---|---|---|
| *A61K 8/27* | (2006.01) | |
| *A61K 8/21* | (2006.01) | |
| *A61K 8/44* | (2006.01) | |
| *A61K 8/73* | (2006.01) | |
| *A61P 31/04* | (2006.01) | |
| *A61Q 11/00* | (2006.01) | |

(52) U.S. Cl.
CPC .................. *A61K 8/21* (2013.01); *A61K 8/27* (2013.01); *A61K 8/442* (2013.01); *A61K 8/735* (2013.01); *A61P 31/04* (2018.01); *A61Q 11/00* (2013.01)

(58) Field of Classification Search
None
See application file for complete search history.

(56) References Cited

U.S. PATENT DOCUMENTS

| | | |
|---|---|---|
| 9,486,396 B2 | 11/2016 | Jaracz et al. |
| 10,058,493 B2 | 8/2018 | Manus et al. |
| 10,342,750 B2 | 7/2019 | Prencipe et al. |
| 10,441,517 B2 | 10/2019 | Prencipe et al. |
| 10,617,620 B2 | 4/2020 | Prencipe et al. |
| 10,744,077 B2 | 8/2020 | Manus et al. |
| 2009/0202454 A1 | 8/2009 | Mello et al. |
| 2015/0313813 A1 | 11/2015 | Rege et al. |
| 2017/0020795 A1 | 1/2017 | Maloney et al. |
| 2018/0015016 A1* | 1/2018 | Huang ................ A61P 1/02 |
| 2018/0021234 A1 | 1/2018 | Prencipe et al. |
| 2019/0038531 A1 | 2/2019 | Rege et al. |
| 2020/0009031 A1 | 1/2020 | Prencipe et al. |
| 2020/0330341 A1 | 10/2020 | Sagel et al. |
| 2020/0337959 A1 | 10/2020 | Manus et al. |
| 2020/0390676 A1 | 12/2020 | Strand et al. |
| 2020/0390677 A1 | 12/2020 | Strand et al. |
| 2020/0390801 A1* | 12/2020 | Strand ................ A61Q 11/00 |

FOREIGN PATENT DOCUMENTS

| | | |
|---|---|---|
| CN | 107205895 A | 9/2017 |
| CN | 110636887 A | 12/2019 |
| WO | 2011/162755 | 12/2011 |
| WO | 2017/000837 | 1/2017 |
| WO | 2018/212771 | 11/2018 |

OTHER PUBLICATIONS

International Search Report and the Written Opinion of the International Searching Authority issued in International Application PCT/CN2022/078926 mailed Jun. 27, 2022.
Wang, et al., May 1994, "Daily Industrial Commodity and Inspection", China Light Industry Press: 62.
Wang, et al., Oct. 1998, "Daily Chemical Products", China Textile & Apparel Press: 70.

* cited by examiner

*Primary Examiner* — Brian Gulledge

(57) ABSTRACT

This invention relates to oral care compositions comprising zinc oxide and zinc citrate, and hyaluronic acid or an alkali metal hyaluronate polymer having a molecular weight greater than 100,000 Da (e.g. from 300 kDa-700 kDa), as well as to methods of using and of making these compositions.

24 Claims, No Drawings

ORAL CARE COMPOSITIONS AND METHODS OF USE

CROSS REFERENCE TO RELATED APPLICATIONS

This application is a United States National Stage application under 35 U.S.C. § 371 of PCT Application No. PCT/CN2022/078926, filed Mar. 3, 2022, which claims priority to Chinese Patent Application 202110248821.7, filed Mar. 5, 2021, the entire contents of each of which are incorporated herein by reference in their entirety.

FIELD

This invention relates to oral care compositions comprising zinc oxide and zinc citrate, and a high-molecular weight hyaluronic acid or an alkali metal hyaluronate polymer (>100,000 Da) (e.g., 300-600 kDA) (e.g., about 480 kDA), as well as to methods of using and of making these compositions.

BACKGROUND

The oral cavity is subject to numerous conditions, including periodontal disease (including gingivitis and periodontitis), dental caries, dental hypersensitivity, halitosis, and oral infections (e.g., fungal or bacterial infections of the oral mucosa).

Dental erosion involves demineralization and damage to the tooth structure due to acid attack from nonbacterial sources. Erosion is found initially in the enamel and, if unchecked, may proceed to the underlying dentin. Generally, saliva has a pH between 7.2 to 7.4. When the pH is lowered and concentration of hydrogen ions becomes relatively high, the tooth enamel can become microscopically etched, resulting in a porous, sponge-like roughened surface. If saliva remains acidic over an extended period, then remineralization may not occur, and the tooth will continue to lose minerals, causing the tooth to weaken and ultimately to lose structure.

Dentinal hypersensitivity is acute, localized tooth pain in response to physical stimulation of the dentine surface as by thermal (hot or cold) osmotic, tactile combination of thermal, osmotic and tactile stimulation of the exposed dentin. Exposure of the dentine, which is generally due to recession of the gums, or loss of enamel, frequently leads to hypersensitivity.

Oral cavity bacteria are the primary cause of dental ailments, including caries, gingivitis, periodontitis, and halitosis. Bacteria associated with dental plaque convert sugar to glucans, which are insoluble polysaccharides that provide plaque with its cohesive properties. Anaerobic bacteria in plaque metabolize sugar to produce acids which dissolve tooth minerals, damaging the enamel and eventually forming dental caries.

Dental plaque is a sticky biofilm or mass of bacteria that is commonly found between the teeth, along the gum line, and below the gum line margins. Dental plaque can give rise to dental caries and periodontal problems such as gingivitis and periodontitis. Dental caries tooth decay or tooth demineralization are caused by acid produced from the bacterial degradation of fermentable sugar.

Zinc is a well-known antimicrobial agent used in toothpaste compositions Zinc is also a well-known essential mineral for human health, and has been reported to help strengthen dental enamel and to promote cell repair. Unfortunately, at higher concentrations, the zinc can impart a notably astringent taste to the composition. There is thus a need for improved antibacterial toothpaste formulations that do not suffer from the drawbacks of conventional compositions.

Hyaluronic acid (also called hyaluronan or hyaluronate) is an anionic, non-sulfated glycosaminoglycan (GAG) widely distributed throughout connective tissues of vertebrates, being the most abundant glycosaminoglycan of higher molecular weight in the extracellular matrix of soft periodontal tissues. Hyaluronan has been found to be effective in treatment of inflammatory processes in medical areas such as orthopedics, dermatology and ophthalmology, and it has been further found to be anti-inflammatory and antibacterial in gingivitis and periodontitis therapy.

While toothpastes and mouthwashes are commonly used to deliver active ingredients (e.g, zinc ions), the effect may be transient as active agents may be quickly washed out of the oral cavity by rinsing, eating or drinking, and/or effective concentrations of agent may be rendered ineffective by rapid dilution by saliva. It is particularly difficult to deliver toothpastes and mouthwashes into the tight periodontal cavity, which lies between the teeth roots and the gum.

Accordingly, there is a need for improved preservative agents for use in oral compositions comprising zinc.

BRIEF SUMMARY

It has been surprisingly found that the inclusion of a particular molecular weight (MW) range of hyaluronic acid or an alkali metal hyaluronate polymer ((e.g, MW>100,000 Da, e.g., 300 kDa-1 MDa),) (e.g., from 300 kDa-600 kDa) (e.g., avg 480 kDA), unexpectedly increases the zinc uptake to the enamel for oral care compositions comprising a zinc oxide and/or zinc citrate, selected at certain concentrations and amounts in the oral cavity of a user. The formulations use comparable amounts of zinc to what is found in current market formulations. However, while comparable amounts of zinc are used in the current invention (i.e., relative to various market formulations), the amount of soluble zinc is believed to be actually increased relative to various market formulations. Without being bound by any theory, it is believed that the presence of certain molecular weight hyaluronic acid (e.g, MW>100,000 Da), (e.g., 300 kDa-1 MDa), (e.g., 300 kDa-600 kDA) (e.g., avg 480 kDA) may help to increase the amount of available soluble zinc, as well as deliver the zinc ions to the enamel, soft tissue and oral mucosa, and which aids in delivery and inhibits bacterial growth in the oral cavity of a user Without being bound by theory, certain molecular weights of hyaluronic acid, (e.g., 300 kDa-1 MDa), (e.g., 300 kDa-600 kDA) (e.g., avg 480 kDA) may produce an increase in the mucoadhesive performance allowing the polymer to possibly interact better with the natural mucin pellicle present at the oral surface and offer improved active delivery.

Further studies also demonstrate that hyaluronic acid (e.g, MW>100,000 Da), (e.g., 300 kDa-1 MDa), (e.g., 300 kDa-600 kDA) (e.g., avg 300 kDa-avg 600 kDA) (e.g., avg 480 kDA) can help reduce the amount of volatile sulfur compound (VSC) in vitro as well as increase the lubrication of toothpaste samples.

In one aspect the invention is an oral care composition (Composition 1.0) comprising:
a. zinc oxide and zinc citrate;
b. hyaluronic acid (HA) or an alkali metal hyaluronate polymer with a molecular weight (MW) greater than 100,000 Da (e.g., molecular weight from 300 kDa-1

MDa), (e.g., molecular weight from 300 kDa-600 kDA), (e.g., a molecular weight from an avg 300 kDa-avg 600 kDA) (e.g., molecular weight of about an avg. 480 kDA).

For example, the invention contemplates any of the following compositions (unless otherwise indicated, values are given as percentage of the overall weight of the composition)

1.1 Composition 1.0, wherein the composition comprises a fluoride source.
1.2 Composition 1.0 or 1.1, wherein the composition comprises a fluoride source selected from: stannous fluoride, sodium fluoride, potassium fluoride, sodium monofluorophosphate, sodium fluorosilicate, ammonium fluorosilicate, amine fluoride (e.g., N'-octadecylt-rimethylendiamine-N,N,N'-tris(2-ethanol)-dihydrofluoride), ammonium fluoride, titanium fluoride, hexafluorosulfate, and combinations thereof.
1.3 The composition of 1.2, wherein the fluoride source is stannous fluoride.
1.4 Any of the preceding compositions wherein the fluoride source is a fluorophosphate.
1.5 Any of the preceding compositions wherein the fluoride source is sodium monofluorophosphate.
1.6 The composition of 1.2, wherein the fluoride source is sodium fluoride.
1.7 Any of the preceding compositions wherein the fluoride source is a fluoride salt present in an amount of 0.1 wt. % to 2 wt. % (0.1 wt %-0.6 wt. %) of the total composition weight (e.g., sodium fluoride (e.g., about 0.32 wt. %) or sodium monofluorophosphate).
1.8 Any of the preceding compositions wherein the fluoride source is sodium fluoride in an amount about 0.32 wt. % based on the weight of the composition.
1.9 Any of the preceding compositions wherein the fluoride source is a soluble fluoride salt which provides fluoride ion in an amount of from 50 to 25,000 ppm (e.g., 750-2000 ppm, e.g., 1000-1500 ppm, e.g., about 1000 ppm, e.g., about 1450 ppm).
1.10 Any of the preceding compositions wherein the fluoride source is sodium fluoride which provides fluoride in an amount from 750-2000 ppm (e.g., about 1450 ppm).
1.11 Any of the preceding compositions wherein the fluoride source is selected from sodium fluoride and sodium monofluorophosphate and which provides fluoride in an amount from 1000 ppm-1500 ppm.
1.12 Any of the preceding compositions wherein the fluoride source is sodium fluoride or sodium monofluorophosphate and which provides fluoride in an amount of about 1450 ppm.
1.13 Any of the preceding compositions wherein the pH is between 7.5 and 10.5, e.g., 9.0 to 10.0, e.g., 9.4.
1.14 Any of the preceding compositions further comprising calcium carbonate.
1.15 The preceding composition, wherein the calcium carbonate is a precipitated calcium carbonate high absorption (e.g., 20% to 30% by weight of the composition) (e.g., 25% precipitated calcium carbonate high absorption).
1.16 The preceding composition, further comprising a precipitated calcium carbonate—light (e.g., about 10% precipitated calcium carbonate—light) (e.g., about 10% natural calcium carbonate).
1.17 Any of the preceding compositions further comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, disodium hydrogenorthophoshpate, monosodium phosphate, pentapotassium triphosphate and mixtures of any of two or more of these, e.g., in an amount of 0.01-20%, e.g., 0.1-8%, e.g., e.g., 0.1 to 5%, e.g., 0.3 to 2%, e.g., 0.3 to 1%, e.g about 0.01%, about 0.1%, about 0.5%, about 1%, about 2%, about 5%, about 6%, by weight of the composition.
1.18 Any of the preceding compositions comprising tetrapotassium pyrophosphate, disodium hydrogenorthophoshpate, monosodium phosphate, and pentapotassium triphosphate.
1.19 Any of the preceding compositions comprising a polyphosphate.
1.20 The preceding composition, wherein the polyphosphate is tetrasodium pyrophosphate.
1.21 The preceding composition, wherein the tetrasodium pyrophosphate is from 0.1-1.0 wt % (e.g., about 0.5 wt %).
1.22 Any of the preceding compositions further comprising an abrasive or particulate (e.g., silica).
1.23 Any of the preceding compositions wherein the composition comprises from 5 to 25% abrasive silica, e.g. from 10 to 20% abrasive silica, e.g., 5 wt %, 10 wt %, 15 wt %, 20 wt % or 25 wt % abrasive silica.
1.24 Any of the preceding compositions wherein the silica is synthetic amorphous silica. (e.g., 1%-28% by wt.) (e.g., 8%-25% by wt.).
1.25 Any of the preceding composition wherein the silica abrasives are silica gels or precipitated amorphous silicas, e.g. silicas having an average particle size ranging from 2.5 microns to 12 microns.
1.26 Any of the preceding compositions further comprising a small particle silica having a median particle size (d50) of 1-5 microns (e.g., 3-4 microns) (e.g., about 5 wt. % Sorbosil AC43 from PQ Corporation, Warrington, United Kingdom).
1.27 Any of the preceding compositions wherein 20-30 wt % of the total silica in the composition is small particle silica (e.g., having a median particle size (d50) of 3-4 microns) and wherein the small particle silica is from 1%-8% (e.g., about 5 wt. %) of the oral care composition.
1.28 Any of the preceding compositions comprising silica wherein the silica is used as a thickening agent, e.g., particle silica.
1.29 Any of the preceding compositions further comprising a nonionic surfactant, wherein the nonionic surfactant is in an amount of from 0.25-5%, e.g, 0.25-2% (e.g., about 0.5% by wt), selected from poloxamers (e.g., poloxamer 407), polysorbates (e.g., polysorbate 20), polyoxyl hydrogenated castor oil (e.g., polyoxyl 40 hydrogenated castor oil), and mixtures thereof.
1.30 Any of the preceding compositions, wherein the poloxamer nonionic surfactant has a polyoxypropylene molecular mass (Mw) of from 3000 to 5000 g/mol and a polyoxyethylene content of from 60 to 80 mol %, e.g., the poloxamer nonionic surfactant comprises poloxamer 407.
1.31 Any of the preceding compositions further comprising glycerin, wherein the glycerin is in a total amount of 25-40% (e.g., about 35%).

1.32 The preceding composition, wherein the glycerin is in an amount of about 35% by wt. of the composition.
1.33 The preceding composition, wherein the glycerin is in an amount of about 26% by wt. of the composition.
1.34 Any of the preceding compositions further comprising sorbitol, wherein the sorbitol is in a total amount of 10-40% (e.g., about 35%).
1.35 Any of the preceding compositions further comprising an additional ingredient selected from: benzyl alcohol, Methylisothizolinone ("MIT"), Sodium bicarbonate, lauryl alcohol, and polyphosphate.
1.36 Any of the preceding compositions wherein the benzyl alcohol is present from 0.1-0.8 wt %, or 0.2 to 0.7 wt %, or from 0.3 to 0.6 wt %, or from 0.4 to 0.5 wt %, e.g. about 0.1 wt. %, about 0.2 wt. %, about 0.3 wt %, about 0.4 wt %, about 0.5 wt %, about 0.6 wt %, about 0.7 wt % or about 0.8 wt %.
1.37 Any of the preceding compositions wherein the benzyl alcohol is about 0.4 wt %.
1.38 Any of the preceding compositions comprising polymer films.
1.39 Any of the preceding compositions comprising flavoring, fragrance and/or coloring.
1.40 The preceding composition, wherein the flavoring agent is sodium saccharin, sucralose, or a mixture thereof.
1.41 Any of the preceding compositions, wherein the composition comprises a thickening agent selected from the group consisting of carboxyvinyl polymers, carrageenan, xanthan, hydroxyethyl cellulose and water-soluble salts of cellulose ethers (e.g., sodium carboxymethyl cellulose and sodium carboxymethyl hydroxyethyl cellulose).
1.42 Any of the preceding compositions, wherein the composition comprises sodium carboxymethyl cellulose (e.g., from 0.5 wt. %-1.5 wt. %) (e.g., 0.8%).
1.43 Any of the preceding compositions comprising from 5%-40%, e.g., 10%-35%, e.g., about 15%, about 25%, about 27%, about 30%, and about 35% water.
1.44 Any of the preceding compositions comprising an additional antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, honokiol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, Zinc Chloride, Zinc Lactate, Zinc Sulfate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.
1.45 Any of the preceding compositions comprising an antioxidant, e.g., selected from the group consisting of Co-enzyme Q10, PQQ, Vitamin C, Vitamin E, Vitamin A, BHT, anethole-dithiothione, and mixtures thereof.
1.46 Any of the preceding compositions comprising a whitening agent.
1.47 Any of the preceding compositions comprising a whitening agent selected from a whitening active selected from the group consisting of peroxides, metal chlorites, perborates, percarbonates, peroxyacids, hypochlorites, and combinations thereof.
1.48 Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.
1.49 Any of the preceding compositions further comprising an agent that interferes with or prevents bacterial attachment, e.g., ethyl lauroyl argininate (ELA) or chitosan.
1.50 Any of the preceding compositions further comprising an amino acid.
1.51 The preceding composition, wherein the amino acid is a basic amino acid.
1.52 The preceding composition, wherein the basic amino acid has the L-configuration (e.g., L-arginine).
1.53 Any of the preceding compositions wherein the basic amino acid is arginine or lysine is in free form.
1.54 Any of the preceding compositions wherein the basic amino acid is provided in the form of a di- or tri-peptide comprising arginine or lysine, or salts thereof.
1.55 Any of the preceding compositions wherein the basic amino acid is arginine, and wherein the arginine is present in an amount corresponding to 0.1% to 15%, e.g., 0.1 wt % to 10 wt %, e.g., 0.1 to 5 wt %, e.g., 0.5 wt % to 3 wt % of the total composition weight, about e.g., 1%, 1.5%, 2%, 3%, 4%, 5%, or 8%, wherein the weight of the basic amino acid is calculated as free form.
1.56 Any of the preceding compositions wherein the amino acid is arginine from 0.1 wt. %-6.0 wt. %. (e.g., about 1.5 wt %).
1.57 Any of the preceding compositions wherein the amino acid is arginine from about 1.5 wt. %.
1.58 Any of the preceding compositions wherein the amino acid is arginine from 4.5 wt. %-8.5 wt. % (e.g., 5.0%).
1.59 Any of the preceding compositions wherein the amino acid is arginine from about 5.0 wt. %.
1.60 Any of the preceding compositions wherein the amino acid is arginine from 3.5 wt. %-9 wt. %.
1.61 Any of the preceding compositions wherein the amino acid is arginine from about 8.0 wt. %.
1.62 Any of the preceding compositions wherein the amino acid is free form arginine.
1.63 Any of the preceding compositions, wherein the ratio of the amount of zinc oxide (e.g., wt. %) to zinc citrate (e.g., wt %) is from 1.5:1 to 4.5:1 (e.g., 2:1, 2.5:1, 3:1, 3.5:1, or 4:1).
1.64 Any of the preceding compositions, wherein the zinc citrate is in an amount of from 0.25 to 1.0 wt % (e.g., 0.25 to 0.75 wt. %, or 0.5 wt. %) and zinc oxide may be present in an amount of from 0.75 to 1.25 wt % (e.g., 1.0 wt. %) based on the weight of the oral care composition.

1.65 Any of the preceding compositions wherein the zinc citrate is about 0.5 wt %.

1.66 Any of the preceding compositions wherein the zinc oxide is about 1.0 wt %.

1.67 Any of the preceding compositions where the zinc citrate is about 0.5 wt % and the zinc oxide is about 1.0 wt %.

1.68 Any of the preceding compositions, wherein the hyaluronic acid or alkali metal hyaluronate polymer has an average molecular weight of 200,000 to 1,500,000 Da, e.g., 300,000 to 1,200,000 Da, or 300,000 to 700,000 Da, or 325,000 to 575,000 or 700,000 to 1,100,000 Da, or 300,000 to 450,000, or 350,000 to 600,000 Da, or 400,000 to 600,000, or 900,000 to 1,100,000 Da, or about 370,000 Da, or about 480,000 Da, or about 550,000 Da, or about 1,000,000 Da.

1.69 The preceding composition, wherein the hyaluronic acid or alkali metal hyaluronate polymer has an average molecular weight of 300,000 to 1.70 The preceding composition, wherein the hyaluronic acid or alkali metal hyaluronate polymer has an average molecular weight of 300,000 to 700,000 Da (e.g., 350 kDa-575 kDa) (e.g., an avg of 350 kDa-avg 575 kDa).

1.71 The preceding composition, wherein the hyaluronic acid or alkali metal hyaluronate polymer has an average molecular weight of 400,000 to 600,000 Da.

1.72 The oral care composition of 1.69, wherein the hyaluronic acid or alkali metal hyaluronate polymer has an average molecular weight of 350 kDa-575 kDa.

1.73 The oral care composition of 1.71 or 1.72, wherein the hyaluronic acid or alkali metal hyaluronate polymer has an average molecular weight of about 480,000 Da (e.g., an avg 480 kDa).

1.74 The oral care composition of 1.71 or 1.72, wherein the hyaluronic acid or alkali metal hyaluronate polymer has an average molecular weight of about 550,000 Da (e.g., an avg 550 kDa).

1.75 The preceding composition, wherein the hyaluronic acid or alkali metal hyaluronate polymer is sodium hyaluronate polymer.

1.76 Any of the preceding compositions, wherein the composition comprises the hyaluronic acid or alkali metal hyaluronate polymer in an amount of 0.01 to 10 wt %, e.g., 0.01 to 5 wt %, 0.05 to 5 wt %, 0.1 to 2 wt %, or 0.1 to 1 wt %, or 0.3 to 0.5 wt %, or about 0.4 wt % based on the weight of the oral care composition.

1.77 The preceding composition, wherein the composition comprises the hyaluronic acid or alkali metal hyaluronate polymer in an amount of 0.05 to 5 wt % based on the weight of the oral care composition.

1.78 The preceding composition, wherein the composition comprises the hyaluronic acid or alkali metal hyaluronate polymer in an amount of 0.025 to 2 wt % based on the weight of the oral care composition.

1.79 Any of the preceding compositions, wherein the composition comprises the hyaluronic acid or alkali metal hyaluronate polymer in an amount of about 0.05% by wt based on the weight of the oral care composition.

1.80 Any of the preceding compositions, wherein the composition comprises the hyaluronic acid or alkali metal hyaluronate polymer in an amount of about 0.1% by wt based on the weight of the oral care composition.

1.81 Any of preceding compositions wherein the composition is ethanol-free 1.82 Any of the preceding compositions comprising:
   a. From 0.5%-1.5% zinc oxide (e.g., 1% by wt.)
   b. From 0.25%-0.75% zinc citrate (e.g., 0.5% by wt.)
   c. From 0.025 to 2 wt % hyaluronic acid (e.g., 0.05% by wt) (e.g., 0.1% by wt.), wherein the molecular weight of hyaluronic acid is from 300,000 to 700,000 Da (e.g., MW of about 480,000 Da) (e.g., e.g., MW of about an avg of 480,000 Da).

1.83 Any of the preceding compositions comprising:
   a. From 0.5%-1.5% zinc oxide (e.g., 1% by wt.)
   b. From 0.25%-0.75% zinc citrate (e.g., 0.5% by wt.)
   c. From 1.0%-2.0% L-arginine (e.g., 1.5% by wt.)
   d. From 0.025 to 2 wt % hyaluronic acid (e.g., 0.05% by wt) (e.g., 0.1% by wt.), wherein the molecular weight of hyaluronic acid is from 300,000 to 700,000 Da (e.g., MW of about 480,000 Da) e.g., e.g., MW of about an avg of 480,000 Da).

1.84 Any of the preceding compositions comprising:
   a. About 1% by wt. zinc oxide
   b. About 0.5% zinc citrate
   c. About 1.5% L-arginine
   d. About 0.05% hyaluronic acid, wherein the molecular weight of hyaluronic acid is from 300,000 to 700,000 Da (e.g., MW of about 480,000 Da) e.g., e.g., MW of about an avg of 480,000 Da).

1.85 Any of the preceding compositions comprising:
   a. About 1% by wt. zinc oxide
   b. About 0.5% zinc citrate
   c. About 1.5% L-arginine
   d. About 0.1% hyaluronic acid, wherein the molecular weight of hyaluronic acid is from 300,000 to 700,000 Da (e.g., MW of about 480,000 Da) e.g., e.g., MW of about an avg of 480,000 Da).

1.86 Any of the preceding compositions effective upon application to the oral cavity, e.g., by rinsing, optionally in conjunction with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity (xiv) reduce erosion, (xv) prevents stains and/or whiten teeth, (xvi) immunize the teeth against cariogenic bacteria; and/or (xvii) promote systemic health, including cardiovascular health, e.g., by reducing potential for systemic infection via the oral tissues.

1.87 Any of the preceding oral compositions, wherein the oral composition may be any of the following oral compositions selected from the group consisting of: a toothpaste or a dentifrice, a mouthwash or a mouth rinse, a topical oral gel, tablet, film, granules, gum, and a denture cleanser.

1.88 A composition obtained or obtainable by combining the ingredients as set forth in any of the preceding compositions.

1.89 Any of the preceding compositions, wherein the amount of hyaluronic acid is in an amount effective to provide a composition where the coefficient of friction is 0.10 (e.g., about 0.08) or less as measured by a tribometer (Bruker UMT), and the coefficient of friction is measured at 1 RPM.

1.90 Any of the preceding compositions comprising an orally acceptable carrier.

1.91 Any of the preceding compositions, wherein the oral care composition is in the form selected from: toothpaste, transparent paste, gel, mouth rinse, spray and chewing gum.

A composition obtained or obtainable by combining the ingredients as set forth in any of the preceding compositions.

A composition for use as set for in any of the preceding compositions.

In another embodiment, the invention encompasses a method to improve oral health comprising applying an effective amount of the oral composition of any of the embodiments set forth above to the oral cavity of a subject in need thereof, e.g., a method to
  i. reduce or inhibit formation of dental caries,
  ii. reduce, repair or inhibit early enamel lesions, e.g., as detected by quantitative light-induced fluorescence (QLF) or electrical caries measurement (ECM),
  iii. reduce or inhibit demineralization and promote remineralization of the teeth,
  iv. reduce hypersensitivity of the teeth,
  v. reduce or inhibit gingivitis,
  vi. promote healing of sores or cuts in the mouth,
  vii. reduce levels of acid producing bacteria,
  viii. to increase relative levels of arginolytic bacteria,
  ix. inhibit microbial bio film formation in the oral cavity,
  x. raise and/or maintain plaque pH at levels of at least pH 5.5 following sugar challenge,
  xi. reduce plaque accumulation,
  xii. treat dry mouth,
  xiii. enhance systemic health, including cardiovascular health, e.g., by reducing potential for systemic infection via the oral tissues,
  xiv. Whiten teeth,
  xv. reduce erosion of the teeth,
  xvi. immunize (or protect) the teeth against cariogenic bacteria and their effects, and/or
  xvii. clean the teeth and oral cavity.

The invention further comprises the use of sodium bicarbonate, MIT (methyl isothiazolinone), and benzyl alcohol and combinations thereof in the manufacture of a Composition of the Invention, e.g., for use in any of the indications set forth in the above method of Composition 1.0, et seq.

DETAILED DESCRIPTION

As used herein, an "oral care composition" refers to a composition for which the intended use includes oral care, oral hygiene, and/or oral appearance, or for which the intended method of use comprises administration to the oral cavity, and refers to compositions that are palatable and safe for topical administration to the oral cavity, and for providing a benefit to the teeth and/or oral cavity. The term "oral care composition" thus specifically excludes compositions which are highly toxic, unpalatable, or otherwise unsuitable for administration to the oral cavity. In some embodiments, an oral care composition is not intentionally swallowed, but is rather retained in the oral cavity for a time sufficient to affect the intended utility. The oral care compositions as disclosed herein may be used in nonhuman mammals such as companion animals (e.g., dogs and cats), as well as by humans. In some embodiments, the oral care compositions as disclosed herein are used by humans.

As used herein, the term "dentifrice" means paste, gel, or liquid formulations unless otherwise specified. The dentifrice composition can be in any desired form such as deep striped, surface striped, multi-layered, having the gel surrounding the paste, or any combination thereof. Alternatively, the oral composition is provided as a dual phase composition, wherein individual compositions are combined when dispensed from a separated compartment dispenser.

As used herein, "hyaluronic acid" is an anionic, non-sulfated glycosaminoglycan (GAG) widely distributed throughout connective tissues of vertebrates, being the most abundant glycosaminoglycan of higher molecular weight in the extracellular matrix of soft periodontal tissues. Hyaluronic acid can exist in its free acid form, or in the form of a salt (such as an alkali metal salt). Hyaluronic acid has important hygroscopic, rheological and viscoelastic properties that fluctuate with changes in temperature, pH, ionic environment, and binding partners. However, these properties are also highly dependent on chain length. Hyaluronic acid can reach over $10^7$ Da in molecular mass, but also exists in multiple smaller forms, referred to as low molecular weight hyaluronan or oligomeric hyaluronan.

Hyaluronan is believed to be effective in treatment of inflammatory processes in medical areas such as orthopedics, dermatology and ophthalmology, and it has been further found to be anti-inflammatory and antibacterial in gingivitis and periodontitis therapy. Due to its tissue healing properties, it has been suggested for use as an adjunct to mechanical therapy in the treatment of periodontitis. Hyaluronan affects endothelial cell proliferation and monolayer integrity, and also has effects on angiogenesis.

Amino Acids

In certain aspects, Compositions 1.0 et seq can include a basic amino acid. The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of 7 or greater.

Accordingly, basic amino acids include, but are not limited to, arginine, lysine, serine, citrullene, ornithine, creatine, histidine, diaminobutanoic acid, diaminoproprionic acid, salts thereof or combinations thereof. In a particular embodiment, the basic amino acids are selected from arginine, citrullene, and ornithine.

In certain embodiments, the basic amino acid is arginine, for example, L-arginine, or a salt thereof.

In certain aspects, the compositions of the invention (e.g., any of Compositions 1.0 et seq) can include a neutral amino acid, which can include, but are not limited to, one or more neutral amino acids selected from the group consisting of alanine, aminobutyrate, asparagine, cysteine, cystine, glutamine, glycine, hydroxyproline, isoleucine, leucine, methionine, phenylalanine, proline, serine, taurine, threonine, tryptophan, tyrosine, valine, and combinations thereof.

The compositions of the invention are intended for topical use in the mouth and so salts for use in the present invention should be safe for such use, in the amounts and concentrations provided. Suitable salts include salts known in the art to be pharmaceutically acceptable salts which are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

In certain embodiments, the basic amino acid is present in an amount corresponding to 0.1% to 15%, e.g., 0.1 wt % to 10 wt %, e.g., 0.1 to 5 wt %, e.g., 0.5 wt % to 3 wt % of the total composition weight, about e.g., 1%, 1.5%, 2%, 3%, 4%, 5%, or 8%, wherein the weight of the basic amino acid is calculated as free form.

Fluoride Ion Source

In certain aspects, the compositions of the invention (e.g., any of Compositions 1.0 et seq) may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., each of which are incorporated herein by reference. Representative fluoride ion sources used with the present invention (e.g., Composition 1.0 et seq.) include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. Where the formulation comprises calcium salts, the fluoride salts are preferably salts wherein the fluoride is covalently bound to another atom, e.g., as in sodium monofluorophosphate, rather than merely ionically bound, e.g., as in sodium fluoride.

Surfactants

The invention may in some embodiments contain anionic surfactants, (e.g., the Compositions of Composition 1.0, et seq.), for example, water-soluble salts of higher fatty acid monoglyceride monosulfates, such as the sodium salt of the monosulfated monoglyceride of hydrogenated coconut oil, sodium cocoglyceride sulfate; higher alkyl sulfates, such as sodium lauryl sulfate; higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or, for example sodium laureth-2 sulfate ($CH_3(CH_2)_{10}CH_2(OCH_2CH_2)_2OSO_3Na$); higher alkyl aryl sulfonates such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. By "higher alkyl" is meant, e.g., C6-30 alkyl. In particular embodiments, the anionic surfactant (where present) is selected from sodium lauryl sulfate and sodium ether lauryl sulfate. When present, the anionic surfactant is present in an amount which is effective, e.g., >0.001% by weight of the formulation, but not at a concentration which would be irritating to the oral tissue, e.g., 1%, and optimal concentrations depend on the particular formulation and the particular surfactant. In one embodiment, the anionic surfactant is present at from 0.03% to 5% by weight, e.g., 1.5%.

In another embodiment, cationic surfactants useful in the present invention can be broadly defined as derivatives of aliphatic quaternary ammonium compounds having one long alkyl chain containing 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants of Composition 1.0, et seq., that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. In a particular embodiment, the composition of the invention comprises a nonionic surfactant selected from polaxamers (e.g., polaxamer 407), polysorbates (e.g., polysorbate 20), polyoxyl hydrogenated castor oils (e.g., polyoxyl 40 hydrogenated castor oil), and mixtures thereof.

Illustrative amphoteric surfactants of Composition 1.0, et seq., that can be used in the compositions of the invention include betaines (such as cocamidopropylbetaine), derivatives of aliphatic secondary and tertiary amines in which the aliphatic radical can be a straight or branched chain and wherein one of the aliphatic substituents contains about 8-18 carbon atoms and one contains an anionic water-solubilizing group (such as carboxylate, sulfonate, sulfate, phosphate or phosphonate), and mixtures of such materials.

The surfactant or mixtures of compatible surfactants can be present in the compositions of the present invention in 0.1% to 5%, in another embodiment 0.3% to 3% and in another embodiment 0.5% to 2% by weight of the total composition.

Flavoring Agents

The oral care compositions of the invention (e.g., any of Compositions 1.0 et seq) can may also include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of 0.01 to 2% by weight.

Chelating and Anti-Calculus Agents

The oral care compositions of the invention also may include one or more chelating agents able to complex calcium found in the cell walls of the bacteria. Binding of this calcium weakens the bacterial cell wall and augments bacterial lysis.

Another group of agents suitable for use as chelating or anti-calculus agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least 0.1 wt. % pyrophosphate ions, e.g., 0.1 to 3 wt 5, e.g., 0.1 to 2 wt %, e.g., 0.1 to 1 wt %, e.g., 0.2 to 0.5 wt %. The pyrophosphates also contribute to preservation of the compositions by lowering the effect of water activity.

Polymers

The oral care compositions of the invention (e.g., any of Compositions 1.0 et seq) can also optionally include one or more polymers, such as polyethylene glycols, polyvinyl methyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water-soluble alkali metal (e.g., potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000 (Mw). These copolymers are available for example as Gantrez AN 139 (M.W. 500,000), AN 1 19 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1 103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorosorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, xanthan gum, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Silica may also be available as a thickening agent, e.g., synthetic amorphous silica. Colloidal magnesium aluminum silicate or finely divided silica can be used as component of the thickening composition to further improve the composition's texture. In certain embodiments, thickening agents in an amount of about 0.5% to about 5.0% by weight of the total composition are used. Thickeners may be present in an amount of from 1 wt % to 15 wt %, from 3 wt % to 10 wt %, 4 wt % to 9 wt %, from 5 wt % to 8 wt %, for example 5 wt %, 6 wt %, 7 wt %, or 8 wt %.

Abrasives

In certain aspects, the compositions of the invention (e.g., any of Compositions 1.0 et seq) may include an abrasive. Natural calcium carbonate is found in rocks such as chalk, limestone, marble and travertine. It is also the principle component of egg shells and the shells of mollusks. The natural calcium carbonate abrasive of the invention is typically a finely ground limestone which may optionally be refined or partially refined to remove impurities. For use in the present invention, the material has an average particle size of less than 10 microns, e.g., 3-7 microns, e.g. about 5.5 microns. For example a small particle silica may have an average particle size (D50) of 2.5-4.5 microns. Because natural calcium carbonate may contain a high proportion of relatively large particles of not carefully controlled, which may unacceptably increase the abrasivity, preferably no more than 0.01%, preferably no more than 0.004% by weight of particles would not pass through a 325 mesh. The material has strong crystal structure, and is thus much harder and more abrasive than precipitated calcium carbonate. The tap density for the natural calcium carbonate is for example between 1 and 1.5 g/cc, e.g., about 1.2 for example about 1.19 g/cc. There are different polymorphs of natural calcium carbonate, e.g., calcite, aragonite and vaterite, calcite being preferred for purposes of this invention. An example of a commercially available product suitable for use in the present invention includes Vicron® 25-11 FG from GMZ.

Precipitated calcium carbonate is generally made by calcining limestone, to make calcium oxide (lime), which can then be converted back to calcium carbonate by reaction with carbon dioxide in water. Precipitated calcium carbonate has a different crystal structure from natural calcium carbonate. It is generally more friable and more porous, thus having lower abrasivity and higher water absorption. For use in the present invention, the particles are small, e.g., having an average particle size of 1-5 microns, and e.g., no more than 0.1%, preferably no more than 0.05% by weight of particles which would not pass through a 325 mesh. The particles may for example have a D50 of 3-6 microns, for example 3.8-4.9, e.g., about 4.3; a D50 of 1-4 microns, e.g. 2.2-2.6 microns, e.g., about 2.4 microns, and a D10 of 1-2 microns, e.g., 1.2-1.4, e.g. about 1.3 microns. The particles have relatively high water absorption, e.g., at least 25 g/100 g, e.g. 30-70 g/100 g. Examples of commercially available products suitable for use in the present invention include, for example, Carbolag® 15 Plus from Lagos Industria Quimica.

In certain embodiments the invention may comprise additional calcium-containing abrasives, for example calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate, and/or silica abrasives, sodium metaphosphate, potassium metaphosphate, aluminum silicate, calcined alumina, bentonite or other siliceous materials, or combinations thereof.

In certain embodiments, the composition may comprise an abrasive silica. Any silica suitable for oral care compositions may be used, such as small particle silica, precipitated silicas, or prophy silicas.

For example, the silica can also be small particle silica (e.g., Sorbosil AC43 from PQ, Warrington, United Kingdom). The composition preferable contains from 5 to 20 wt % small particle silica, or for example 10-15 wt %, or for example 5 wt %, 10 wt %, 15 wt % or 20 wt % small particle silica.

In another embodiment, the abrasive may be high cleaning precipitated silica having a pellicle cleaning ratio (PCR) of greater than 85 when tested at 20% loading is known in the art as high cleaning silica. Typically, high cleaning silica also has a mean particle size $d_{50}$ of from 5 to 15 µm and an oil absorption of from 40 to 120 cm$^3$/100 g silica. The cleaning efficacy of the precipitated silica is expressed using the pellicle cleaning ratio (PCR). This is typically measured at 20% silica loading. The high cleaning silica preferably has a PCR value of greater than 85. The efficacy of the precipitated silica can also be expressed with reference to its abrasive characteristic using the radioactive dentin abrasion (RDA). Ideally, RDA values for an oral composition should be below about 250 to protect tooth enamel/dentin. Methods of performing PCR and RDA are described in e.g., U.S. Pat. Nos. 5,939,051 and 6,290,933 and "In Vitro Removal of Stain With Dentifrice", G. K. Stookey et al., J. Dental Research, Vol. 61, pages 1236-9, November 1982." Typically, the precipitated silica has a mean particle size $d_{50}$ of from 5 to 15 µm and an oil absorption of from 40 to 120 cm$^3$/100 g silica. Examples of precipitated silica having a mean particle size $d_{50}$ of from 5 to 15 µm and an oil absorption of from 40 to 120 cm$^3$/100 g silica including commercially available silicas such as Zeodent®103 and Zeodent® 105 (Huber Silica Americas).

The composition preferable contains from 5 to 20 wt % high cleaning precipitated silica, or for example 10-15 wt %, or for example 5 wt %, 10 wt %, 15 wt % or 20 wt % high cleaning precipitated silica.

The composition may also comprise an abrasive silica having an acid pH in the composition. For example, prophy silica available from Grace, offered as Sylodent™, can be used. The acidic silica abrasive is included in the dentifrice components at a concentration of about 2 to about 35% by weight; about 3 to about 20% by weight, about 3 to about 15% by weight, about 10 to about 15% by weight. For example, the acidic silica abrasive may be present in an amount selected from 2 wt. %, 3 wt. %, 4% wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %.

A commercially available acidic silica abrasive is Sylodent 783 available from W. R. Grace & Company, Baltimore, Md. Sylodent 783 has a pH of 3.4-4.2 when measured as a 5% by weight slurry in water. For use in the present invention, the silica material has an average particle size of less than 10 microns, e.g., 3-7 microns, e.g. about 5.5 microns.

Water

Water is present in the oral compositions of the invention (e.g., any of Compositions 1.0 et seq). Water, employed in the preparation of commercial oral compositions should be deionized and free of organic impurities. Water commonly makes up the balance of the compositions and includes 5% to 45%, e.g., 10% to 20%, e.g., 25-35%, by weight of the oral compositions. This amount of water includes the free water which is added plus that amount which is introduced with other materials such as with sorbitol or silica or any components of the invention. The Karl Fischer method is a one measure of calculating free water.

Humectants

In certain aspects, the compositions of the invention (e.g., any of Compositions 1.0 et seq) may incorporate a humectant to reduce evaporation and also contribute towards preservation by lowering water activity. Certain humectants can also impart desirable sweetness or flavor to the compositions. The humectant, on a pure humectant basis, generally includes 15% to 70% in one embodiment or 30% to 65% in another embodiment by weight of the composition.

Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the compositions herein.

pH Adjusting Agents

In certain aspects, the compositions of the invention (e.g., any of Compositions 1.0 et seq) can contain a buffering agent. Examples of buffering agents include anhydrous carbonates such as sodium carbonate, sesquicarbonates, bicarbonates such as sodium bicarbonate, silicates, bisulfates, phosphates (e.g., monopotassium phosphate, monosodium phosphate, disodium phosphate, dipotassium phosphate, tribasic sodium phosphate, sodium tripolyphosphate, pentapotassium tripolyphosphate, phosphoric acid), citrates (e.g. citric acid, trisodium citrate dehydrate), pyrophosphates (sodium and potassium salts, e.g., tetrapotassium pyrophosphate) and combinations thereof. The amount of buffering agent is sufficient to provide a pH of about 5 to about 9, preferable about 6 to about 8, and more preferable about 7, when the composition is dissolved in water, a mouthrinse base, or a toothpaste base. Typical amounts of buffering agent are about 5% to about 35%, in one embodiment about 10% to about 30%, in another embodiment about 15% to about 25%, by weight of the total composition.

The present invention in its method aspect involves applying to the oral cavity a safe and effective amount of the compositions described herein.

The compositions and methods according to the invention (e.g., Composition 1.0 et seq) can be incorporated into oral compositions for the care of the mouth and teeth such as toothpastes, transparent pastes, gels, mouth rinses, sprays and chewing gum.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1

Soluble Zinc Measurement

The ability of hyaluronic acid to increase soluble zinc concentration is tested in simple solutions. Soluble zinc concentration is measured and the results are detailed in Table 1 below. The procedure to measure soluble zinc:

1. Weigh 5 g of each zinc-HA or zinc-chitosan solution into a 50 mL centrifuge tube. Repeat in triplicate.
2. Add 15 g of DI H2O. Vortex the solution to completely mix the total solution.
3. Centrifuge the samples at 12,500 rpm for 10 minutes. Remove 1 mL of the supernatant and place it in a 15 mL centrifuge tube.
4. Add 0.5 mL of concentrated nitric acid and leave the samples at room temperature for 30 minutes.
5. Then add 3.5 mL of DI $H_2O$ and vortex.

Data obtained from the simple solutions analyzed in the method above is detailed in Table 1:

TABLE 1

| Sample | Zinc Detected (ppm) |
|---|---|
| A: Zinc oxide (control)[1] | 0.62 |
| B: Polymer (control)[2] | N/A |
| C: Zinc oxide[1] + HA (molecular weight 1 MDa)[3] | 0.77 |
| D: Zinc oxide[1] + HA (molecular weight avg 480 kDA)[3] | 2.12 |
| E: Zinc oxide[1] + HA (molecular weight < 10 kDA)[3] | 5.05* |

[1]Zinc oxide present at 0.25% by wt. in samples A, C-E
[2]Polymer contains 0.1% chitosan and 0.1% HA (1 MDa), no zinc.
[3]"HA" represents hyaluronic acid. HA is added at 0.1% by wt.
4. Sample A contains 49.75% by wt deionized water. Sample B contains 49.80% by wt. deionized water. Samples C-E contain 49.65% deionized water.
*p < 0.05 vs all other samples (ANOVA + Tukey)

Example 2

Next, the ability of hyaluronic acid to increase zinc uptake in in vitro tests is measured. Zinc uptake in a vitro skin method is measured as followed:

Procedure for the Vitro Skin Assay:
I. Preparation (Day 0)
  A. Use a hole punch to cut vitro skin from bulk sheets into disks 7 mm in diameter.
  B. Fill hydration chamber with a 15%/85% glycerin/deionized water solution (44 g glycerin, 256 g water). Hydrate ~30 vitro skin disks overnight in hydration chamber by placing them on the screen racks.
II. Next Day (Day 1)
  A. Acquire 10 mL parafilm stimulated saliva centrifuged at 8000 rpm for 10 minutes.
  B. Remove and transfer the salivary supernatant into a Max 10 speed mixer cup. Transfer the vitro skin disks into the 10 mL of salivary supernatant and incubate for 2 hours at 37° C. on an orbital shaker, rotating at 120 rpm allowing for pellicle formation.
III. Vitro Skin Treatment (Day 1)
  A. Place 5 mL of each zinc-HA or zinc-chitosan solution to be tested in a Max 10 speed mixer cup.
  B. Place 3 vitro skin disks into each speed mixer cup making sure the samples are fully immersed in the suspension.
  C. Incubate the five cups for 1 hour at 37° C. on an orbital shaker (120 rpm).
  D. Remove the vitro skin disks from the solutions and gently wash by dipping the skin into deionized water (20 mL) 3 times. Some of the substance may continue to stick to the vitro skin depending on how mucoadhesive it is to the vitro skin. Replace wash water with every new sample.
  E. Place each vitro skin in a clean 15 mL conical tube and label.
  F. Add 0.5 mL of concentrated nitric acid to each 15 mL tube. Make sure that the vitro skin is fully submerged in the nitric acid (sometimes they have a tendency to stick to the sides of the tube).
  G. Let the samples sit at room temperature overnight to digest the vitro skin in the acid.
IV. Next Day (Day 2) A. Add 4.5 mL of deionized water to each of the 15 mL tubes and vortex to mix.

Zinc uptake in the vitro skin method is detailed in Table 2:

TABLE 2

| Sample | Zinc Detected (ppm) |
|---|---|
| A: Zinc oxide (control)[1] | 2.3 |
| B: Polymer (control)[2] | N/A |
| C: Zinc oxide[1] + HA (molecular weight of 1 MDa)[3] | 22.8* |
| D: Zinc oxide[1] + HA (molecular weight avg 480 kDa)[3] | 85.6*,† |
| E: Zinc oxide[1] + HA (molecular weight < 10 kDa)[3] | 13.2 |

[1]Zinc oxide present at 0.25% by wt. in samples A, C-E
[2]Polymer contains 0.1% chitosan and 0.1% HA (1 MDa)
[3]"HA" represents hyaluronic acid. HA is added at 0.1% by wt.
4. Sample A contains 49.75% by wt deionized water. Sample B contains 49.80% by wt. deionized water. Samples C-E contain 49.65% deionized water.
*p < 0.05 vs zinc oxide control (ANOVA + Tukey)
†p < 0.05 vs samples C and E Accordingly, from the data presented in Tables 1 and 2 above, samples with HA (avg 480 kDA) surprisingly increase delivering available zinc to the oral mucosa when measured against both higher and lower molecular weight hyaluronic acid samples. However, HA samples with 1 MDa and avg 480 kDA hyaluronic acid were both statistically different from the zinc control confirming an improved zinc delivery from the addition of HA. Additionally, all samples with hyaluronic acid demonstrate improved zinc solubility relative to control samples without hyaluronic acid (Table 1).

Example 3

Zinc Uptake by In-Vitro Hard Tissue

Various formulations with zinc and hyaluronic acid are tested in an in-vitro hard tissue model designed to demonstrate the zinc retention capacity on hydroxyapatite discs.

Dentifrice Formulations (amounts listed as % by wt. of the total composition)

TABLE 3

| Description | Compound F | Compound G | Compound H |
|---|---|---|---|
| Humectants | 52 | 52 | 52 |
| Anionic Surfactant | 5.7 | 5.7 | 5.7 |
| Amphoteric Surfactant | 1.25 | 1.25 | 1.25 |
| Flavoring/Fragrance/Coloring Agent | 2.16 | 2.16 | 2.16 |
| Thickening agent | 0.8 | 0.8 | 0.8 |
| Polymer | 0.3 | 0.3 | 0.3 |
| Alkali pyrophosphate salt | 0.5 | 0.5 | 0.5 |
| Synthetic Amorphous Precipitated Silica | 5 | 5 | 5 |
| Silica | 16 | 16 | 16 |
| Benzyl Alcohol | 0.1 | 0.1 | 0.1 |
| Zinc Citrate | 0.5 | 0.5 | 0.5 |
| Zinc Oxide | 1.0 | 1.0 | 1.0 |
| Sodium Fluoride - USP, EP | 0.32 | 0.32 | 0.32 |
| Hyaluronic acid (avg. MW: 480 kDA) | — | 0.05 | 0.1 |
| Demineralized Water | q.s. | q.s. | q.s. |
| Total Amount | 100% | 100% | 100% |

Dentifrice Formulations:

(amounts listed as % by wt. of the total composition)

TABLE 4

| Description | Compound I | Compound J | Compound K |
|---|---|---|---|
| Humectants | 35 | 35 | 35 |
| Anionic Surfactant | 5.7 | 5.7 | 5.7 |
| Amphoteric Surfactant | 1.25 | 1.25 | 1.25 |
| Nonionic Surfactant | 0.5 | 0.5 | 0.5 |
| Flavoring/Fragrance/Coloring Agent | 2.57 | 2.57 | 2.57 |
| Thickening agent | 0.8 | 0.8 | 0.8 |
| Polymer | 0.4 | 0.4 | 0.4 |
| Alkali pyrophosphate salt | 0.5 | 0.5 | 0.5 |
| Arginine | 1.5 | 1.5 | 1.5 |
| Silica | 22 | 22 | 22 |
| Benzyl Alcohol | 0.4 | 0.4 | 0.4 |
| Zinc Citrate | 0.5 | 0.5 | 0.5 |
| Zinc Oxide | 1.0 | 1.0 | 1.0 |
| Sodium Fluoride - USP, EP | 0.32 | 0.32 | 0.32 |
| Hyaluronic acid (avg. MW 480 kDA) | — | 0.05 | 0.1 |
| pH adjusting agent | 0.35 | 0.35 | 0.35 |
| Demineralized Water | q.s. | q.s. | q.s. |
| Total Amount | 100% | 100% | 100% |

Table 5 and Table 6 below demonstrated that formulas G, H, J and K—which all contain some amount of hyaluronic acid—can significantly improve zinc retention on HAP Disc compared to equivalent formulations without HA. Note, statistically there is no significant difference between toothpastes with 0.05% and 0.1% HA:

TABLE 5

| Formula | Zinc/µg/substrate |
|---|---|
| Compound F | 105.36 |
| Compound G | 125.03* |
| Compound H | 136.85* |

*Statistically significant vs. Compound F

TABLE 6

| Formula | Zinc/µg/substrate |
|---|---|
| Compound I | 119.07 |
| Compound J | 181.40* |
| Compound K | 199.47* |

*Statistically significant vs. Compound I

Example 4

Volatile Sulfur Compound (VSC) Reduction Efficacy

The below tables demonstrate the results of the evaluation of in-vitro bacterial generated Volatile Sulfur Compound (VSC) reduction efficacy in Compound G vs. Compound F. In general, methyl mercaptan is a representative ingredient of volatile sulfur compound (VSC), which can be used as the marker for the quantitative measurement of mouth odor through gas chromatography-flame photometric detector technology. Hydroxyapatite (HAP) is incubated with whole saliva to develop pellicles followed by the treatment of testing and control dentifrice slurries. After rinsing, the treated disks are transferred to headspace vials and incubated with VSC solution to mimic mouth odor (VSC) generation. The methyl mercaptan in headspace is measured through gas chromatography-flame photometric detector and the results are intended to determine the product efficacy in mouth odor reduction.

Table 6 demonstrates methyl mercaptan measurement by gas chromatograph to evaluate VSC reduction efficacy. As demonstrated in Table 6, Compound G (Table 3, 0.05% HA) shows a significant decrease in methyl mercaptan reduction when measured against similar toothpaste (Compound F) which do not contain hyaluronic acid. Without being bound by theory, the surprising increase may relate to the increased availability of zinc ion in these formulations.

TABLE 7

| Formula | Log (integrated hydrogen sulfide area) |
|---|---|
| Compound F | 6.53 |
| Compound G | 6.12* |

Example 5

Antibacterial Efficacy

In this Example, the experimental methodology used is the Biofilm

Growth Inhibition University of Manchester Model. The protocol for this model is as follows:

a.
- a. (1) Dental plaque is collected from four healthy volunteers and pooled together as inoculum. The Optical Density of the inoculum is matched to 0.3 absorbance at 610 nm b. (2) Sterile hydroxyapatite (HAP) disks were incubated under anaerobic conditions at 37° C. for 24 hours with 1 mL of sterile artificial saliva (with 0.01 weight % sucrose) and 1 mL of pooled saliva in a 24 well microplate.
c. (3) For each test dentifrice (and for each control) a treatment solution of 1 part dentifrice: 2 parts sterile distilled water by weight is made up. Each freshly prepared treatment solution is added to three wells and allowed to contact the HAP disk therein for 10 minutes.
d. (4) The liquid phase of each well is then removed and is replaced by 2 mL sterile artificial saliva.
e. (5) The disks were then maintained at 37° C. under anaerobic conditions for 8 days.
f. (6) At intervals of 2, 4 and 8 days, the disks were collected aseptically and transferred to half-strength pre-reduced thioglycollate medium (4.5 ml per disk).
g. (7) 100μ of the dilution 10-4, 10-5 and 10-6 were plated in duplicates for each disk on Neomycin/Vancomycin (NV) Agar for Total Gram-negative Anaerobes.
h. (8) The plates were surface-spread using a sterile spreader and were incubated anaerobically at 37° C. for 72 hours, after which time the number of colonies on each plate is counted.

The log 10 CFU/ml (where CFU=colony forming units) for each test dentifrice or control is calculated. A lower Log 10 CFU/ml indicates that the dentifrice tested has greater efficacy in inhibiting biofilm growth.

The results obtained using the Biofilm Growth Inhibition University of Manchester Model methodology (above) are shown in Table 8, with the average log 10 CFU/ml obtained from the disk incubated for 8 days in step 6 of the method. Results for dentifrice formulas 1-7, subject to the evaluation, are listed in Table 8.

TABLE 8

| Formula | Avg. Log RLU | Statistical Group |
|---|---|---|
| 1: (Commercially available formula - No HA, no Zinc) | 5.46 | A |
| 2: (Zinc citrate 0.5%, Zinc Oxide 1.0%, 0.2% Benzyl Alcohol) | 5.32 | B |
| 3: (Zinc citrate 0.5%, Zinc Oxide 1.0%, 0.05% hyaluronic acid (avg. MW: 480 kDA)) | 5.29 | B, C |
| 4: (Zinc citrate 0.5%, Zinc Oxide 1.0%, 0.1% hyaluronic acid (avg. MW: 480 kDA)) | 5.23 | B, C |
| 5: (Zinc citrate 0.5%, Zinc Oxide 1.0%, 0.05% hyaluronic acid, 0.2% benzyl alcohol) | 5.22 | B, C |
| 6: (Zinc citrate 0.5%, Zinc Oxide 1.0%) | 5.20 | B, C |
| 7: (Zinc citrate 0.5%, Zinc Oxide 1.0%, 0.1% hyaluronic acid (avg. 480 kDA), 0.2% benzyl alcohol) | 5.18 | C |

*Means that do not share a letter are significantly different.

As demonstrated in Table 8, Formula 7 (which includes: Zinc citrate 0.5%, Zinc Oxide 1.0%, 0.1% hyaluronic acid, 0.2% benzyl alcohol) performed significantly better with respect to antibacterial efficacy than a similarly situated toothpaste (Formula 2) which does not contain any hyaluronic acid.

Example 6

Determining Lubrication Effect and Hyaluronic Acid

To test the lubrication effect of hyaluronic acid, toothpaste with 1% zinc oxide and 0.5% zinc citrate were made into slurries containing either 0.05% or 0.1% hyaluronic acid (avg. MW 480 kDa). The protocol for the assay is as follows:
a. Slurries of 1 part TP and 1 part tap water were prepared.
b. The slurries were poured on a Vitro skin substrate.
c. The coefficient of friction is measured with increasing RPM from 0.1 to 20, while the probe is at 15 mm from the center, and the normal force is 1 N.
d. After slurry test, the substrates were rinsed with 10 mL water, and then, the coefficient of friction is measured the same way.
e. The tests were repeated three times for all samples With increasing amounts of hyaluronic acid, the coefficient of friction decreased (e.g., enhanced lubrication). When rinsed, 0.1% hyaluronic acid samples demonstrate higher lubrication compared to the control without any hyaluronic acid. However, 0.05% hyaluronic acid demonstrates similar lubrication to the control sample in rinsed samples. The average Coefficient of Friction ("COF") of rinsed samples at 1 RPM: both 0% HA and 0.05% HA samples had an average COF of 0.12 (±0.02). The average Coefficient of Friction ("COF") of rinsed samples at 1 RPM with 0.1% HA is 0.08 (±0.02). As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

While the present invention has been described with reference to embodiments, it will be understood by those skilled in the art that various modifications and variations may be made therein without departing from the scope of the present invention as defined by the appended claims.

The invention claimed is:
1. An oral care composition comprising:
a. zinc oxide and zinc citrate; and
b. hyaluronic acid (HA) or an alkali metal hyaluronate polymer with an average molecular weight ranging from about 300,000 Da to about 700,000 Da.
2. The oral care composition of claim 1, wherein the composition comprises a fluoride source.
3. The oral care composition of claim 1, wherein the composition comprises a fluoride source selected from: stannous fluoride, sodium fluoride, potassium fluoride, sodium monofluorophosphate, sodium fluorosilicate, ammonium fluorosilicate, amine fluoride, ammonium fluoride, titanium fluoride, hexafluorosulfate, and combinations thereof.
4. The oral care composition of claim 1, wherein the oral care composition further comprises an amino acid.
5. The oral care composition of claim 4, wherein the amino acid is a basic amino acid.
6. The oral care composition of claim 5, wherein the basic amino acid has the L-configuration.
7. The oral care composition of claim 6, wherein the basic amino acid is arginine, and wherein the arginine is present in an amount corresponding to 0.1% to 15 wt. %, wherein the weight percentage of arginine is calculated as free form.
8. The oral care composition of claim 7, wherein the arginine is present in an amount of about 1.5 wt. %.

9. The oral care composition of claim 1, wherein the weight ratio of the amount of zinc oxide (e.g., wt. %) to zinc citrate (e.g., wt %) is from 1.5:1 to 4.5:1.

10. The oral care composition of claim 1, wherein the zinc citrate is present in an amount of from 0.25 to 1.0 wt. % and the zinc oxide may be is present in an amount of from 0.75 to 1.25 wt. %, based on the weight of the oral care composition.

11. The oral care composition of claim 1, wherein the hyaluronic acid or alkali metal hyaluronate polymer has an average molecular weight of 325,000 to 575,000 Da.

12. The oral care composition of claim 1, wherein the hyaluronic acid or alkali metal hyaluronate polymer has an average molecular weight of 300,000 to 450,000 Da.

13. The oral care composition of claim 1, wherein the hyaluronic acid or alkali metal hyaluronate polymer has an average molecular weight of about 480,000 Da.

14. The oral care composition of claim 1, wherein the hyaluronic acid or alkali metal hyaluronate polymer has an average molecular weight of about 550,000 Da.

15. The oral care composition of claim 1, wherein the hyaluronic acid or alkali metal hyaluronate polymer is present in an amount of about 0.01 to about 10 wt. %, based on the weight of the oral care composition.

16. The oral care composition of claim 15, wherein the hyaluronic acid or alkali metal hyaluronate polymer is present in an amount of about 0.05 to about 5 wt. %, based on the weight of the oral care composition.

17. The oral care composition of claim 16, wherein the hyaluronic acid or alkali metal hyaluronate polymer is present in an amount of about 0.025 to about 2 wt. %, based on the weight of the oral care composition.

18. The oral care composition of claim 1, wherein the composition comprises the hyaluronic acid or alkali metal hyaluronate polymer is present in an amount of about 0.05 wt. % by wt, based on the weight of the oral care composition.

19. The oral care composition of claim 1, wherein the composition comprises the hyaluronic acid or alkali metal hyaluronate polymer is present in an amount of about 0.1 wt. %, by wt based on the weight of the oral care composition.

20. The oral care composition claim 1, wherein the composition comprises:
c. from about 0.5 to about 1.5 wt. % of zinc oxide;
d. from about 0.25 to about 0.75 wt. % of zinc citrate;
e. from about 0.025 to about 2 wt. % of hyaluronic acid, wherein the average molecular weight of hyaluronic acid is from 300,000 to 700,000 Da.

21. The oral care composition of claim 1 comprising:
f. from about 0.5 to about 1.5 wt. % of zinc oxide;
g. from about 0.25 to about 0.75 wt. % of zinc citrate;
h. from about 1 to about 2 wt. % of L-arginine;
i. from about 0.025 to about 2 wt. % of hyaluronic acid, wherein the molecular weight of average hyaluronic acid is from 300,000 to 700,000 Da.

22. The oral care composition of claim 1, wherein the oral composition may be any of the following oral compositions selected from the group consisting of: a toothpaste or a dentifrice, a mouthwash or a mouth rinse, a topical oral gel, and a denture cleanser.

23. The oral care composition of claim 1, wherein the composition is obtained or obtainable by combining the ingredients in said oral care composition.

24. A method to improve oral health comprising applying an effective amount of the oral composition of claim 1 set forth above to the oral cavity of a subject in need thereof, wherein the method is effective to:
  i. reduce or inhibit formation of dental caries,
  ii. reduce, repair or inhibit early enamel lesions,
  iii. reduce or inhibit demineralization and promote remineralization of the teeth,
  iv. reduce hypersensitivity of the teeth,
  V. reduce or inhibit gingivitis,
  vi. promote healing of sores or cuts in the mouth,
  vii. reduce levels of acid producing bacteria,
  viii. to increase relative levels of arginolytic bacteria,
  ix. inhibit microbial bio film formation in the oral cavity,
  X. raise and/or maintain plaque pH at levels of at least pH 5.5 following sugar challenge,
  xi. reduce plaque accumulation,
  xii treat dry mouth,
  xiii. enhance systemic health, including cardiovascular health,
  xiv. Whiten teeth,
  XV. reduce erosion of the teeth,
  xvi. immunize (or protect) the teeth against cariogenic bacteria and their effects, and/or
  xvii. clean the teeth and oral cavity.

* * * * *